(12) United States Patent
Chami

(10) Patent No.: US 8,845,516 B2
(45) Date of Patent: Sep. 30, 2014

(54) LIGATOR

(75) Inventor: Salah Chami, Birkerød (DK)

(73) Assignee: EndoChoice, Inc., Alpharetta, GA (US)

( * ) Notice: Subject to any disclaimer, the term of this patent is extended or adjusted under 35 U.S.C. 154(b) by 1613 days.

(21) Appl. No.: 11/919,775

(22) PCT Filed: May 9, 2005

(86) PCT No.: PCT/DK2005/000312
§ 371 (c)(1),
(2), (4) Date: Nov. 1, 2007

(87) PCT Pub. No.: WO2006/119762
PCT Pub. Date: Nov. 16, 2006

(65) Prior Publication Data
US 2009/0131748 A1    May 21, 2009

(51) Int. Cl.
*A61B 1/00* (2006.01)
*A61B 17/12* (2006.01)
*A61B 1/04* (2006.01)
*A61B 19/00* (2006.01)
*A61B 17/00* (2006.01)

(52) U.S. Cl.
CPC . *A61B 17/12013* (2013.01); *A61B 2017/12018* (2013.01); *A61B 2019/4815* (2013.01); *A61B 2017/00296* (2013.01)
USPC ............................ 600/104; 600/106; 600/127

(58) Field of Classification Search
USPC .................. 600/104, 106, 127, 131, 154, 129; 606/139–141
See application file for complete search history.

(56) References Cited

U.S. PATENT DOCUMENTS

| 5,320,630 | A  |   | 6/1994  | Ahmed |
|---|---|---|---|---|
| 5,398,844 | A  |   | 3/1995  | Zaslavsky |
| 5,462,559 | A  | * | 10/1995 | Ahmed ........................ 606/140 |
| 5,788,715 | A  | * | 8/1998  | Watson et al. ................ 606/140 |
| 6,051,003 | A  |   | 4/2000  | Chu |
| 6,059,798 | A  |   | 5/2000  | Tolkoff |
| 6,066,145 | A  | * | 5/2000  | Wurster ........................ 606/141 |
| 6,149,659 | A  | * | 11/2000 | Ahmed ........................ 606/140 |
| 6,235,040 | B1 |   | 5/2001  | Chu |
| 6,565,578 | B1 | * | 5/2003  | Peifer et al. .................... 606/139 |
| 6,730,101 | B1 | * | 5/2004  | Peifer et al. .................... 606/140 |
| 6,893,393 | B2 | * | 5/2005  | Carrillo ........................ 600/154 |
| 6,929,603 | B2 | * | 8/2005  | Durell ............................ 600/173 |
| 6,974,466 | B2 | * | 12/2005 | Ahmed et al. ................ 606/140 |

(Continued)

FOREIGN PATENT DOCUMENTS

| WO | WO97/16120 | 5/1997 |
|---|---|---|
| WO | WO/02/45595 | 6/2002 |
| WO | WO0245595 | 6/2002 |

*Primary Examiner* — Alireza Nia
(74) *Attorney, Agent, or Firm* — Thomas | Horstemeyer, LLP

(57) ABSTRACT

An apparatus applicable for the ligation of internal tissue in a created or natural cavity in animals or in the human body, for example varicose veins in the gullet or a duodenal diverticulum, by means of an elastic band (19) while observing the ligations through an endoscope. The apparatus includes an automatic trigger unit (1) mounted firmly on the handle of the endoscope which can release a number of elastic bands (19) with the aid of a single-stranded trigger cord (11). Only a single elastic band (19) is released for each ligation thereby establishing a one-man-operated apparatus.

25 Claims, 4 Drawing Sheets

(56) References Cited

U.S. PATENT DOCUMENTS

| | | | |
|---|---|---|---|
| 7,150,752 B2* | 12/2006 | Suzuki et al. | 606/141 |
| 7,220,227 B2* | 5/2007 | Sasaki et al. | 600/154 |
| 2003/0233043 A1* | 12/2003 | Windheuser et al. | 600/434 |
| 2006/0135846 A1* | 6/2006 | Hunt | 600/104 |
| 2006/0259041 A1* | 11/2006 | Hoffman et al. | 606/139 |
| 2007/0265493 A1* | 11/2007 | Zirps et al. | 600/104 |
| 2008/0015613 A1* | 1/2008 | Saeed et al. | 606/139 |
| 2008/0091218 A1* | 4/2008 | Richardson | 606/140 |

* cited by examiner

LIGATOR

This application claims the benefit of PCT/DK2005/000312 filed May 9, 2009, which is hereby incorporated by reference in its entirety.

This invention relates to medical ligating instruments, and more particularly to devices used to ligate body tissue in a created or natural cavity in animals or in the human body, for example varicose veins in the gullet or a duodenal diverticulum, by means of individual elastic bands while observing the ligations through an endoscope.

BACKGROUND OF THE DISCLOSURE

It takes supreme effort to maneuver an endoscope while you ligate internal tissue in a created or natural cavity in animals or in the human body, for example varicose veins in the gullet or a duodenal diverticulum, by means of individual elastic bands while observing the ligations through an endoscope if the surgeon is supposed to maneuver the endoscope and activate the release of a number of elastic bands all by himself. Therefore it is common practice for an assistant to help the surgeon while he maneuvers the endoscope and releases elastic bands during the actual ligation.

Furthermore, it is very inconvenient for the patient when the endoscope is lead into the gullet or other openings of the human body. Therefore it most advantageous to perform a safe and quick operation.

For known ligating instruments related to the present invention, the trigger unit is not firmly fixed at the distal end the endoscope, see for example U.S. Pat. No. 6,149,659. Therefore you must hold the trigger unit firmly with one hand, and with the other hand you can draw the trigger cord to obtain the ligation of the desired varix or diverticulum. A third and eventually a fourth hand are needed to hold and maneuver the endoscope.

For known ligating instruments related to the present invention, two or more trigger cords are used in releasing the rubber bands, see, for example U.S. Pat. No. 6,235,040 and WO 9716120. The consequence of having two or more trigger cords is that the cords can cross one another and squeeze, for example a varix, which easily can result in bleeding and put the patient's health at risk and make the treatment very troublesome.

SUMMARY OF THE DISCLOSURE

Therefore it is an object of the present invention to provide an improved ligating instrument where the surgeon can very quickly and with great safety perform the operation by himself using an automatic trigger unit according to the invention, which further can lead to reduction of staff in connection with the surgery.

Further it is an object of the present invention to provide an improved ligating instrument where the great risk of squeezing body tissue, for example a varix in the gullet, is eliminated in connection with the ligation.

The first mentioned object according to the present invention can be achieved using a ligating instrument, which includes a trigger unit mounted firmly on the endoscope. Hereby is produced a one-man-operated endoscope, where the surgeon has complete control over the endoscope.

A grip of the trigger unit on the endoscope at a joint between the tube and the handle of the endoscope can be secured by means of a U-shaped bracket on a connecting part.

To enable gripping of the trigger unit on the endoscope at the joint between the tube and the handle of the endoscope no matter the diameter of the endoscope, the connecting part can be provided with a fixture, for example VELCRO™ tape.

When the U-shaped bracket is connected with the trigger unit by means of one or more toggle joints, one can secure a socket-shaped nozzle to the proximal end of the accessory channel of the endoscope and afterwards turn the U-shaped bracket to fasten the bracket between the tube and the handle of the endoscope.

It has surprisingly been revealed that it is possible to overcome the drawbacks that occur when trigger cords cross one another, which can lead to squeezing of internal tissue, such as a varix, that consequently can lead to severe bleeding, when you have a single-stranded trigger cord at the distal end of the trigger cord.

The use of a single-stranded trigger cord implies an adequate large size of the knots or beads because a single knot or bead on the distal end of the trigger cord is responsible for guiding an elastic band over the distal end of a bush and releasing it for the ligation of specific internal tissue.

When the trigger cord is manufactured of metal wire, preferably twisted metal wire, at least two essential advantages are achieved because twisted metal wire is simultaneously rigid and very flexible. Therefore the surgeon has an optimal touch with the firing of elastic bands. Because of the high strength of metal wires, a very tiny dimension can be used which leaves the optimal space in the accessory channel for flushing if bleeding occurs during the ligation.

The use of the one-man-operated, automatic, dual-fixed, trigger unit according to the invention provides an adapted up-winding of the trigger cord corresponding to the release of a single elastic band at the distal end of the endoscope. The up-winding can be achieved by simultaneously turning the revolving parts to the built-in stop at their extreme position where the release of an elastic band takes place, and the simultaneous compressing of a built-in spring is performed. After the release of an elastic band has taken place, the revolving part at which the proximal end of the trigger cord is attached leaves its engagement with the part that has the winding track and automatically returns to its starting point while the trigger cord is coiled up on the winding track.

When the trigger unit has sounded a signal at the extreme position of the revolving parts, the surgeon instantly becomes aware that the release of an elastic band has taken place, after which the surgeon instantly can let go of the revolving parts, after which the tensed revolving part automatically returns to its starting point. Hereby is obtained the obvious advantage that the operation can be performed in a shorter amount of time, which means less discomfort for the patient.

For flushing if bleeding occurs during the ligation, the trigger unit according to the invention has an integrated canal upon which a flexible injection tube can be mounted to the ligator. When the injection tube is mounted, the surgeon can flush the fiber optic from any angle at the proximal end of the endoscope by the means of a syringe.

By manufacturing a bush according to the invention, there is provided a retainer for the elastic bands by the use of a single-stranded trigger cord. The use of a single-stranded trigger cord leads to a more safe operation for the patient. Moreover, the bush loaded with the elastic bands is considerably easier and therefore less expensive to produce.

The bush loaded with elastic bands is prepared to be connected with the distal end of an endoscope after joining the trigger cord from the bush with the trigger cord from the trigger unit via the accessory channel of the endoscope.

DETAILED DESCRIPTION OF THE PREFERRED EMBODIMENTS

Figure 1:
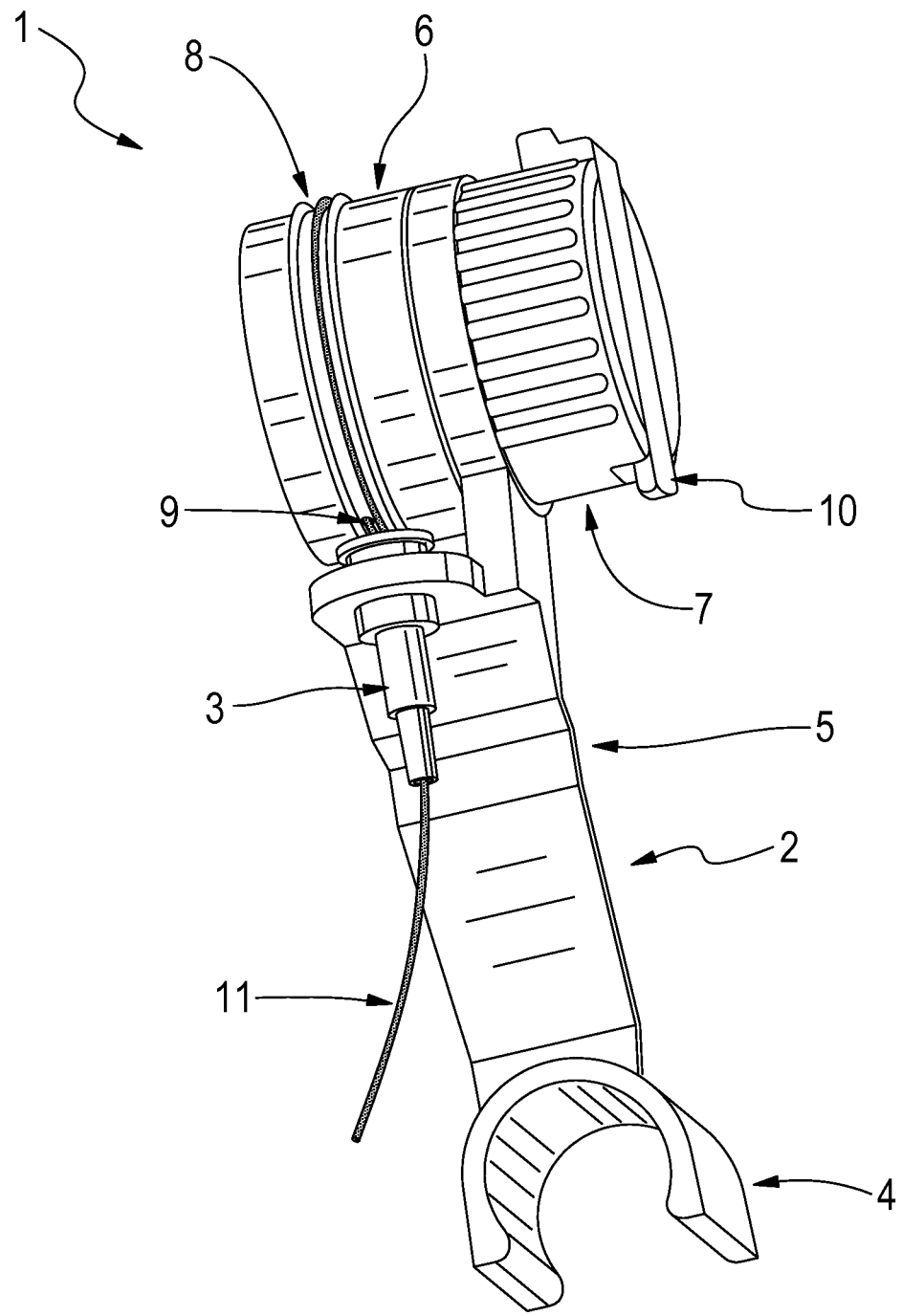
FIG. 1 is a perspective view of a trigger unit.

FIG. 1 illustrates a trigger unit, which is generally identified with the reference number 1. The trigger unit 1 has a connecting part 2 on which a socket-shaped nozzle 3 is mounted. Further, a U-shaped bracket 4 is mounted on the connecting part 2 by means of a toggle joint 5. Two revolving parts 6 and 7 of the trigger unit 1 can revolve together on a shaft, not shown, since the shaft is lead through a bedding, not shown, in the connecting part 2. The first revolving part 6 has a winding track 8 which is meant for the guiding and winding of a trigger cord 11. The other revolving part 7 has a built-in spring, not shown, which after the release of an elastic band 19 ensures that the revolving part 7 leaves its engagement with the revolving part 6 and automatically returns to its starting point, while the revolving part 6 ensures automatic winding of the trigger cord 11 on the winding track 8. From the socket-shaped nozzle 3, the trigger cord 11 is lead through a hole 9 in the winding track 8 and into revolving part 6 and revolving part 7, and further to a cord clamp 10 where the cord is secured. The cord clamp 10 is shown in its locked position in FIG. 1.

Figure 2:
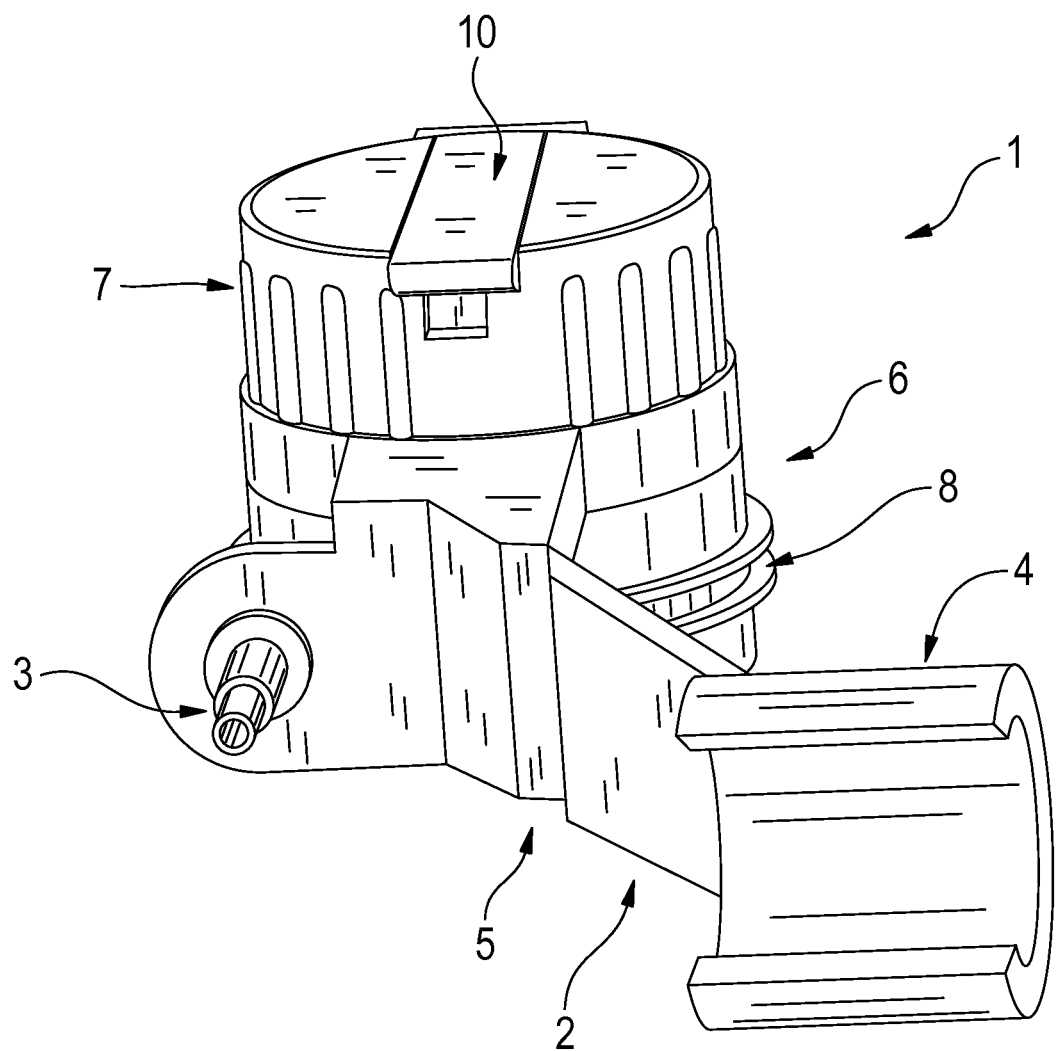
FIG. 2 is a perspective view of a trigger unit where a trigger cord is guided into the trigger unit.

FIG. 2 illustrates the trigger unit 1 as seen from below, where the U-shaped bracket 4 is connected with the trigger unit 1 by means of one or more toggle joints 5.

Figure 3:
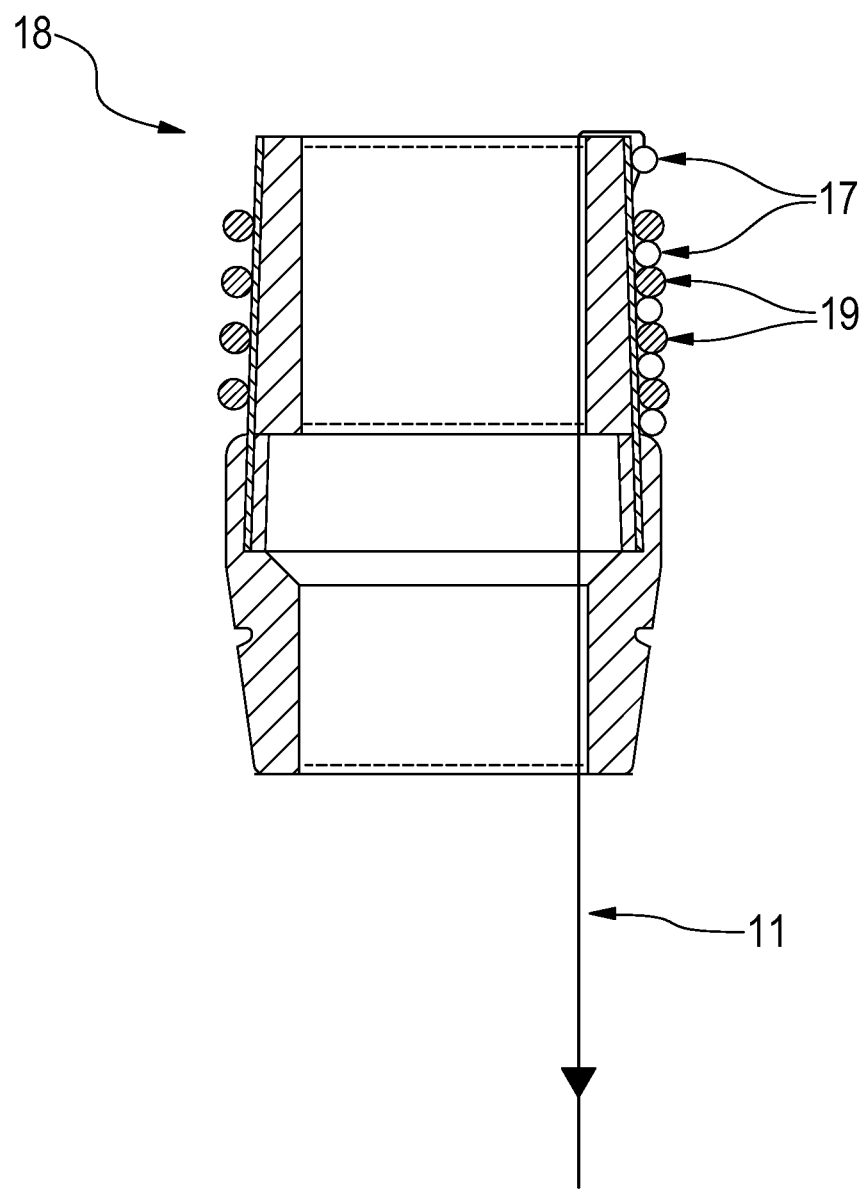
FIG. 3 is a longitudinal section through a bush upon which is placed a flexible trigger cord having beads and elastic bands.

FIG. 3 illustrates how the distal end of the trigger cord 11 is provided with a number of beads 17. The trigger cord 11 is, as shown, guided through a bush 18 and folded backwards on the outer end of the bush. The bush 18 is mounted on the distal end of the tube 14 of the endoscope. Elastic bands 19 are placed on the bush 18 so that they encircle the bush with the trigger cord 11 in between the beads 17.

If the trigger cord 11 is pulled inwards into the tube of the endoscope 4, meaning downwards in FIG. 3, the beads 17 on the distal end of the trigger cord 11 will guide the elastic bands 19 over the distal end of the bush 18 and successively release the elastic bands 19.

Pulling of the trigger cord 11 into the tube of the endoscope 4 is achieved when the proximal end of the trigger cord 11 is fastened on the trigger unit 1 by means of the cord clamp 10. The revolving parts 6 and 7 revolve from the starting position to their extreme position where there is a built-in stop, during which the release of an elastic band 19 takes place.

Figure 4:
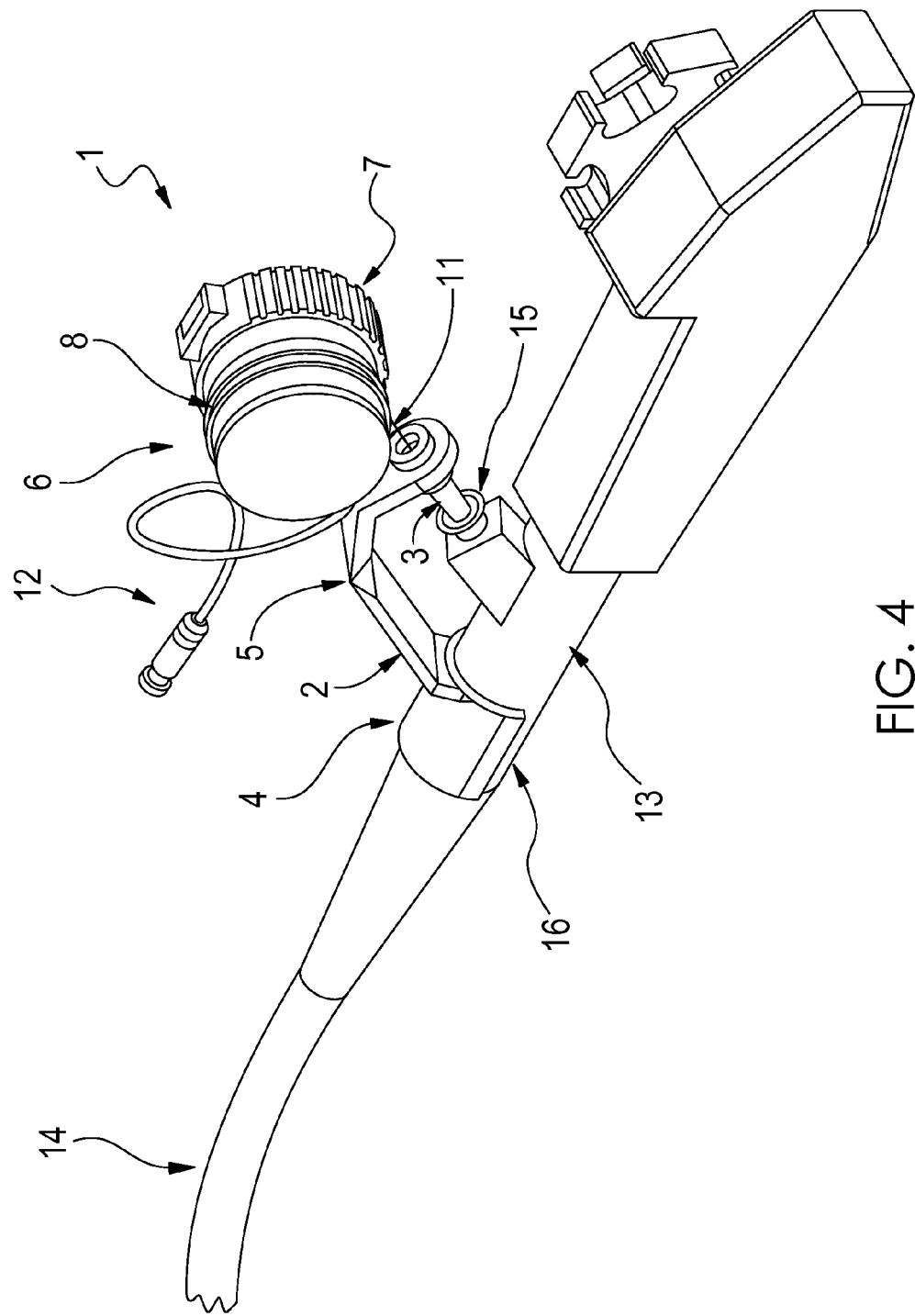
FIG. 4 is a perspective view of a trigger unit according to the present invention shown firmly mounted on the proximal end of an endoscope.

FIG. 4 illustrates the trigger unit 1 mounted on the handle 13 of an endoscope. The trigger cord 11 is guided from the proximal opening 15 of the endoscope to the trigger unit 1, on which a flexible injection tube 12 can be fixed. The dual-fixed trigger unit 1 is partly fixed by anchoring the socket-shaped nozzle 3 of the trigger unit 1 into the accessory channel 15 of the endoscope and partly by the connecting unit 2 of the trigger unit 1 via the U-shaped bracket 4.

In operation, the distal end of the endoscope is supplied with a loaded bush 18 and is guided over a varicose vein while the vein is observed through the endoscope or on a monitor. If it is necessary, the varicose vein can be sucked into the bush 18 using a pump.

When the varicose vein is in place, as can be observed through the endoscope or on a monitor, an elastic band 19 can be released. The band 19 then places itself around the varicose vein, which leads to halt of blood circulation and consequently to necrosis of the tissue. When the distal end of the endoscope is provided with a loaded bush 18, one or more varicose veins can be treated in the same manner as long as there is an elastic band 19 on the bush 18. In this way, individual elastic bands 19 can be placed around separate varicose veins.

The invention claimed is:

1. A ligator for use with an endoscope having a body, a flexible tube extending from the body, and an accessory channel extending through the body and the tube, the ligator comprising:

a trigger unit including a revolving part, a built-in spring that applies an opposing spring force to the revolving part when it is turned, and a built-in stop that limits turning of the revolving part to an extreme position beyond which it can no longer be turned;

a connecting part extending from the trigger unit and including an elongated arm adapted to directly grip the body of the endoscope at a portion of the body located between an opening to the accessory channel and the flexible tube;

a nozzle extending from the connecting part, the nozzle being adapted to be received within the accessory channel of the endoscope;

a bush adapted to mount to an end of the tube of the endoscope, the bush supporting elastic bands to be deployed for ligation; and a trigger cord connected at a first end to the revolving part of the trigger unit and connected at a second end to the bush;

wherein turning of the revolving part from a starting position causes up-winding of the trigger cord, wherein a single elastic band is deployed when the revolving part reaches the built-in stop at the extreme position, and wherein the revolving part automatically returns to the starting position under the force of the built-in spring when the revolving part is released, at which point it is ready to be turned again to deploy the next elastic band.

2. The ligator of claim 1, wherein the revolving part includes a cord clamp that secures the first end of the trigger cord to the revolving part.

3. The ligator of claim 1, wherein the trigger unit includes a further, separate revolving part.

4. The ligator of claim 3, wherein both revolving parts can be turned in the same direction.

5. The ligator of claim 3, wherein the further, separate revolving part includes a winding track that guides the trigger cord.

6. The ligator of claim 1, wherein the connecting part is elongated.

7. The ligator of claim 1, wherein the connecting part comprises a U-shaped bracket adapted to grip the handle of the endoscope.

8. The ligator of claim 1, wherein the connecting part comprises at least one toggle joint.

9. The ligator of claim 1, wherein the nozzle is socket shaped.

10. The ligator of claim 1, wherein the bush is cylindrical.

11. The ligator of claim 1, wherein the bush comprises an outer surface and defines an inner passage.

12. The ligator of claim 11, wherein the elastic band is wrapped around the outer surface of the bush.

13. The ligator of claim 12, wherein the trigger cord extends from the outer surface and into the inner passage of the bush.

14. The ligator of claim 13, wherein the trigger cord comprises beads provided along its length, a bead being provided behind the elastic band wrapped around the outer surface of the bush.

15. The ligator of claim 13, wherein the trigger cord extends from the bush, through the nozzle, and into the revolving part.

16. The ligator of claim 1, further comprising a flexible injection tube.

17. The ligator of claim 1, wherein the revolving part is adapted to cause deployment of the elastic band when it is turned from a starting position to an extreme position, beyond which it can no longer be turned.

18. The ligator of claim 17, wherein the revolving part is further adapted to sound a signal at the extreme position to signal a user that release of the elastic band has occurred.

19. The ligator of claim 17, wherein the revolving part is further adapted to automatically return to the starting position after being released once the elastic band has been deployed.

20. A ligator for use with an endoscope having a body, a flexible tube extending from the body, and an accessory channel extending through the body and the tube, the ligator comprising:
　a trigger unit including a revolving part that can be turned, a built-in spring that applies an opposing spring force to the revolving part when it is turned, and a built-in stop that limits turning of the revolving part to an extreme position beyond which it can no longer be turned;
　a connecting part extending from the trigger unit and including an elongated arm adapted to mount the trigger unit to the body of the endoscope, the elongated arm comprising a U-shaped bracket adapted to grip the body of the endoscope;
　a nozzle extending from the connecting part, the nozzle being adapted to be received within the accessory channel of the endoscope;
　a cylindrical bush adapted to mount to an end of the tube of the endoscope, the bush comprising an outer surface and defining an inner passage, the bush supporting multiple elastic bands that are wrapped about it outer surface; and
　a single trigger cord connected at a first end to the revolving part of the trigger unit and connected at a second end to the bush, wherein the trigger cord extends from the outer surface of the bush, through the inner passage, through the nozzle, and into the revolving part, the trigger cord comprising beads provided along its length, one bead being positioned behind each elastic band wrapped around the outer surface of the bush;
　wherein the revolving part is adapted to cause deployment of a single elastic band when the revolving part is turned from a starting position to the built-in stop at the extreme position, and to then automatically return to the starting position under the force of the built-in spring when the revolving part is released, at which point it is ready to be turned again to deploy the next elastic band;
　wherein the elastic bands are deployable using only the single trigger cord and the ligator comprises no other cords or wires.

21. The ligator of claim 20, wherein the revolving part is further adapted to sound a signal at the extreme position to signal a user that release of the single elastic band has occurred.

22. The ligator of claim 20, wherein the revolving part is further adapted to automatically return to the starting position after being released once the single elastic band has been deployed.

23. The ligator of claim 20, further comprising a further revolving part adapted to coil up the trigger cord.

24. A ligator for use with an endoscope having a tube and an accessory channel, the ligator comprising:
　a trigger unit including a revolving part, a built-in spring that applies an opposing spring force to the revolving part when it is turned, and a built-in stop that limits turning of the revolving part to an extreme position beyond which it can no longer be turned;
　a nozzle adapted to be received within the accessory channel of the endoscope;
　a bush adapted to mount to an end of the tube of the endoscope, the bush supporting elastic bands to be deployed for ligation; and
　a single trigger cord connected at a first end to the revolving part of the trigger unit and connected at a second end to the bush;
　wherein the revolving part is adapted to cause deployment of a single elastic band when the revolving part is turned from a starting position to the built-in stop at the extreme position, and to automatically return to the starting position under the force of the built-in spring after being released, at which point it is ready to be turned again to deploy the next elastic band;
　wherein the elastic bands are deployable using only the single trigger cord and the ligator comprises no other cords or wires.

25. The ligator of claim 24, wherein the revolving part is further adapted to sound a signal at the extreme position to signal a user that release of the elastic band has occurred.

\* \* \* \* \*